US009249064B2

(12) United States Patent
Kumar et al.

(10) Patent No.: US 9,249,064 B2
(45) Date of Patent: Feb. 2, 2016

(54) STORAGE OF INTERMITTENT RENEWABLE ENERGY AS FUEL USING CARBON CONTAINING FEEDSTOCK

(75) Inventors: Challapalli Naga Kiran Kumar, Satyanarayanapuram (IN); Kim-Chinh Tran, Gardabaer (IS); Omar Freyr Sigurbjornsson, Reykjavik (IS); Jonathan Whitlow, Melbourne Beach, FL (US); Kathleen Alexander, Corvallis, OR (US)

(73) Assignee: CRI, EHF, Gardabaer (IS)

( * ) Notice: Subject to any disclaimer, the term of this patent is extended or adjusted under 35 U.S.C. 154(b) by 751 days.

(21) Appl. No.: 13/510,729

(22) PCT Filed: Nov. 22, 2010

(86) PCT No.: PCT/IS2010/050009
§ 371 (c)(1),
(2), (4) Date: Jun. 25, 2012

(87) PCT Pub. No.: WO2011/061764
PCT Pub. Date: May 26, 2011

(65) Prior Publication Data
US 2013/0137783 A1 May 30, 2013

(30) Foreign Application Priority Data

Nov. 20, 2009 (IS) .............................................. 8862
Aug. 16, 2010 (IS) .............................................. 8923

(51) Int. Cl.
| C07C 27/00 | (2006.01) |
| C07C 1/02 | (2006.01) |
| C10K 3/06 | (2006.01) |
| C10G 2/00 | (2006.01) |
| C10J 3/00 | (2006.01) |

(52) U.S. Cl.
CPC ... *C07C 1/02* (2013.01); *C10G 2/32* (2013.01); *C10J 3/00* (2013.01); *C10K 3/06* (2013.01); *C10J 2300/0916* (2013.01); *C10J 2300/0959* (2013.01); *C10J 2300/0976* (2013.01); *C10J 2300/1284* (2013.01); *C10J 2300/1612* (2013.01); *C10J 2300/1643* (2013.01); *C10J 2300/1646* (2013.01); *C10J 2300/1659* (2013.01); *C10J 2300/1684* (2013.01); *Y02E 20/16* (2013.01); *Y02E 50/32* (2013.01)

(58) Field of Classification Search
CPC ............ C07C 1/02; C10K 3/006; C10G 2/32; C10J 3/00; C10J 2300/1684; C10J 2300/0916; C10J 2300/0959; C10J 2300/1284; C10J 2300/1612; C10J 2300/1659; Y02E 20/16; Y02E 50/32
USPC ................................................. 518/700, 702
See application file for complete search history.

(56) References Cited

U.S. PATENT DOCUMENTS

| 4,059,076 A | 11/1977 | Kosaka et al. |
| 4,087,259 A | 5/1978 | Fujitani et al. |
| 4,418,236 A | 11/1983 | Cornelius et al. |
| 4,788,369 A | 11/1988 | Marsh et al. |
| 4,844,837 A | 7/1989 | Heck et al. |
| 4,910,227 A | 3/1990 | Brown et al. |
| 5,342,702 A | 8/1994 | MacGregor |
| 5,416,245 A | 5/1995 | MacGregor et al. |
| 5,500,449 A | 3/1996 | Benham et al. |
| 5,602,289 A | 2/1997 | van Dijk |
| 5,648,582 A | 7/1997 | Schmidt et al. |
| 5,974,826 A | 11/1999 | Baldwin et al. |
| 6,237,284 B1 | 5/2001 | Erickson |
| 6,254,807 B1 | 7/2001 | Schmidt et al. |
| 6,265,453 B1 | 7/2001 | Kennedy |
| 6,306,917 B1 | 10/2001 | Bohn et al. |
| 6,736,955 B2 | 5/2004 | Shaw |
| 8,198,338 B2 | 6/2012 | Shulenberger et al. |
| 8,506,910 B2 | 8/2013 | Singh et al. |
| 2002/0120017 A1 | 8/2002 | Bohn et al. |

(Continued)

FOREIGN PATENT DOCUMENTS

| DE | 19522083 | 10/1996 |
| DE | 20320020 | 5/2004 |

(Continued)

OTHER PUBLICATIONS

Inui et al., Effective Conversion of Carbon Dioxide to Gasoline, 1992, Energy Convers. Mgmt, vol. 33, No. 5-8, pp. 513-520.

(Continued)

*Primary Examiner* — Jafar Parsa
(74) *Attorney, Agent, or Firm* — Charles M. Yeomans, Esq.; Pietragallo Gordon Alfano Bosick & Raspanti, LLP

(57) ABSTRACT

A method and system for converting intermittent renewable energy and renewable carbonaceous feedstock to non-intermittent renewable electrical and thermal energy, storing it as fuels and chemicals and using it to capture and re-use or dispose of $CO_2$ emissions. The system in a preferred embodiment is realized through the generation of non-intermittent renewable electricity utilizing intermittent renewable energy sources along with gaseous fuel from renewable carbonaceous feedstock, producing oxygen and hydrogen from non-intermittent renewable electricity and utilizing the oxygen and hydrogen as required for gasification of renewable carbonaceous feedstock to produce gaseous fuel stream and gaseous intermediate stream, utilizing the gaseous intermediate stream to produce renewable fuels and renewable chemicals, and utilizing oxygen for oxy-rich combustion for concentrating $CO_2$ emissions for easy processing, re-use and disposal.

43 Claims, 4 Drawing Sheets

(56) References Cited

U.S. PATENT DOCUMENTS

| | | |
|---|---|---|
| 2004/0216465 A1 | 11/2004 | Sheppard et al. |
| 2004/0265158 A1 | 12/2004 | Boyapati et al. |
| 2006/0211777 A1 | 9/2006 | Severinsky |
| 2007/0244208 A1 | 10/2007 | Shulenberger et al. |
| 2008/0072496 A1 | 3/2008 | Yogev et al. |
| 2008/0081998 A1 | 4/2008 | Pan et al. |
| 2008/0084457 A1 | 4/2008 | Hibi et al. |
| 2008/0084463 A1 | 4/2008 | Kawase |
| 2008/0115415 A1 | 5/2008 | Agrawal et al. |
| 2008/0303348 A1 | 12/2008 | Witters |
| 2008/0319093 A1 | 12/2008 | Olah et al. |
| 2010/0280135 A1* | 11/2010 | Doty .............................. 518/703 |

FOREIGN PATENT DOCUMENTS

| | | |
|---|---|---|
| JP | 57126434 | 8/1982 |
| JP | 03200734 | 9/1991 |
| WO | 03003559 A1 | 5/2003 |
| WO | 03/066779 A1 | 8/2003 |
| WO | 2005/005312 A2 | 1/2005 |
| WO | 2006/099573 A1 | 9/2006 |
| WO | 2007/076363 A2 | 5/2007 |
| WO | 2007/108014 A1 | 9/2007 |
| WO | 2008/130260 | 10/2008 |
| WO | 2008/137815 A1 | 11/2008 |
| WO | 2009/019159 A2 | 2/2009 |
| WO | 2009025003 A2 | 2/2009 |
| WO | 2009/076042 A1 | 6/2009 |
| WO | 2009073422 A1 | 6/2009 |
| WO | 2009/087060 A2 | 7/2009 |
| WO | 2009/087210 A2 | 7/2009 |
| WO | 2009/091437 A1 | 7/2009 |

OTHER PUBLICATIONS

Schliesinger, M.D. et al., Fisher-Tropsch Synthesis in Slurry Phase, Engineering and Process Development, vol. 43 (6): 1474-1479 (1951).

* cited by examiner

STORAGE OF INTERMITTENT RENEWABLE ENERGY AS FUEL USING CARBON CONTAINING FEEDSTOCK

CROSS-REFERENCE TO RELATED APPLICATIONS

This application is a U.S. National Stage Application under 35 U.S.C. Section 371 of PCT International Application No. PCT/IS2010/050009, filed on Nov. 22, 2010, claiming the benefit of Iceland Application No. 8862, filed Nov. 20, 2009, and Iceland Application No. 8923, filed Aug. 16, 2010.

FIELD OF THE INVENTION

The present invention relates to renewable energy utilization and storage along with $CO_2$ recycling or disposal via production of fuels and chemicals through synthesis gas intermediate. Specifically, the disclosure relates to the recycling of industrial $CO_2$ emissions for the non-intermittent production of renewable fuels and chemicals through gaseous intermediates utilizing intermittent renewable energy and renewable carbonaceous feedstock.

BACKGROUND OF THE INVENTION

The global mean surface temperature increase from the 1860s to 1994 is between 0.3 to 0.6° C. and the temperature rise by the year 2100 is expected to be in the range of 1 to 3.5° C., with a best estimate of 2° C. Carbon dioxide is one of the greenhouse gases that enhances radiative forcing and contributes to this global warming. The concentration of $CO_2$ in Earth's atmosphere prior to industrialization was 270-280 ppmv while in 1994 it had risen to 354 ppmv and is expected to double within the next century. Burning of fossil fuels, the main source of $CO_2$, produces around 21.3 billion tons of carbon dioxide per year, but it is estimated that natural processes can only absorb about half of that amount, so there is a net increase of 10.65 billion tons of atmospheric carbon dioxide per year. World energy consumption was growing about 2.3% per year and world carbon dioxide emissions are expected to increase by 1.8 percent annually between 2004 and 2030. Halmann et al. describes the effects of a global temperature increase to include: "(1) a rise in sea level, due to melting of the glaciers and the Antarctic ice caps and (2) increasing desert formation in the tropical zone".

Energy Information Administration estimated that in 2006 primary sources of energy consisted of petroleum 36.8%, coal 26.6%, and natural gas 22.9%, amounting to an 86% share for fossil fuels. The Reserves-to-production ratio (RPR or R/P) is the remaining amount of a non-renewable resource, expressed in years. Based on International Energy Outlook 2009 from EIA, R/P ratios of the world's main fossil energy sources are: Crude oil—40 to 44 years, Natural Gas—55 to 57 years, Coal (2006)—137 years. The R/P ratio might decrease drastically over time as the consumption of many resources typically increases as the population grows and becomes more prosperous. This leaves a huge challenge for mankind to search for alternative energy sources. This trend of rapid consumption of fossil fuels brings two major challenges to mankind—global warming and depletion of fossil energy resources.

Halmann et al. and George Olah et al. proposes 3 main strategies to solve the problems of global warming and diminishing fossil resources: 1) Increase Energy efficiency to reduce $CO_2$ and fossil fuel use 2) Use of renewable energy to replace fossil energy usage in both the fields of electricity generation and liquid fuel utilization 3) Direct reduction of $CO_2$ through capture, storage or re-use. Efficiency of current processes consuming fossil fuels can be improved to increase the amount of useful energy per unit of $CO_2$ emitted. Halmann et al. in 1999 concludes that by 2050 a 60% reduction in energy consumption and $CO_2$ emissions is possible with improved energy efficiency from mid-1970s. The study does however, not consider the rise in population and thus the foreseeable increase in energy demand. Population rose from 4 billion in 1975 to 6.8 billion by 2008, with expected population rise to 10 billion by 2050. Thus, savings due to increased energy efficiency can only extend the availability of needed and accessible fossil fuels in the relative short term.

Increased utilization of renewable energy is another strategy as it produces very little or zero carbon emissions and is replenished naturally. In 2006, about 18% of global final energy consumption came from renewable energy, with 13% coming from traditional biomass, and 3% from hydro power. The storages and flows of renewable energy on the planet are very large relative to human needs. The amount of solar energy intercepted by the Earth every minute is greater than the amount of energy the world uses in fossil fuels each year. The energy in the winds that blow across the United States each year could produce more than 16 billion GJ of electricity—more than one and one-half times the electricity consumed in the United States in 2000. According to Hoffert et al., stabilization of $CO_2$ at twice the preindustrial concentration in the atmosphere requires that by the year 2050, 100-300% of today's global power (~10 TW) come from carbon-emission-free sources. Main shortcomings of renewables are their low areal power densities. 10 TW from biomass (power density ~0.6 W $m^{-2}$) requires greater than 10% of Earth's land surface, comparable to all of human agriculture. Photovoltaic and wind energy (power density ~15 $W_e$ $m^{-2}$) need less land, but other materials can be limiting. For solar energy, the electrical equivalent of 10 TW (3.3 $TW_e$) requires a surface array of 220,000 sq. km. However, all the PV cells shipped from 1982 to 1998 would only cover ~3 $km^2$. A massive, but not insurmountable, scale-up is required to get 10 to 30 TW equivalents. Also, energy from most of the renewable sources is harnessed dynamically and will not be as useful as fossil carbon until it can be stored and transported with similar ease. With intermittent renewables such as solar and wind, the output may be fed directly into an electricity grid. At penetrations below 20% of the grid demand, this does not severely change the economics; but beyond about 20% of the total demand, external storage will become important. Current and emerging technologies in the field of energy storage, according to the National Renewable Energy Laboratory of United States, include: batteries, hydrogen, compressed air energy storage (CAES), flywheels, pumped hydropower, super capacitors, and superconducting magnetic energy. Of particular interest to the present disclosure, PCT/EP2008/059866, submitted by Werner Leonhard, discloses a method for achieving energy sustainability by converting energy into hydrogen, and using this gas as the means for energy storage. But hydrogen has very low volumetric energy density which creates problems for physical storage. Also, concerns of safety and the requirement of massive infrastructural changes hinder the use of hydrogen for energy storage. Though much work is also being done on energy storage through batteries, the energy densities of these storage techniques are not sufficient to replace fossil energy sources. For example today's lead acid batteries can store about 0.1 megajoules per kilogram, or about 500 times less than crude oil. Those batteries, of course, could be improved, but any battery based on the standard lead-oxide/sulfuric acid chemistry is limited by foundational thermodynamics to less than 0.7 mega-joules per kilogram.

One approach to support global warming mitigation is direct reduction of $CO_2$ through Carbon Capture and Storage (CCS), a process comprising of the separation of $CO_2$ from industrial and energy-related sources, transport to a storage location and long-term isolation from the atmosphere. In most scenarios for stabilization of atmospheric greenhouse gas concentrations between 450 and 750 ppmv $CO_2$ the economic potential of CCS would amount to 220-2,200 $GtCO_2$ (60-600 GtC) cumulatively, which would mean that CCS contributes 15-55% to the cumulative mitigation effort worldwide until 2100, averaged over a range of baseline scenarios. Uncertainties in these economic potential estimates are significant. For CCS to achieve such an economic potential, several hundreds to thousands of $CO_2$ capture systems would need to be installed over the coming century, each capturing some 1-5 $MtCO_2$ per year. The actual implementation of CCS, as for other mitigation options, is likely to be lower than the economic potential due to factors such as environmental impacts, risks of leakage and the lack of a clear legal framework or public acceptance. CCS is a costly process, leading to reduced plant efficiencies and is not economically favorable unless incentives are provided.

Another approach for direct $CO_2$ reduction is carbon capture and re-use. Commercial applications of $CO_2$ reuse are currently limited to refrigeration for food (PCT/US1999/5974826 Novak et al), carbonated beverages, enhanced oil recovery and chemicals. In 1980, the total US market consumption of 2.3 million tons carbon represents only 0.18% of the US total emission. Halmann et al. concludes that as a sink for $CO_2$ the market demand would have to grow by at least two factors of 10 to become a major factor in reducing man made $CO_2$. Another $CO_2$ reduction scheme is disclosed in PCT/US2001/6237284 by Stewart E. Erickson where $CO_2$ storage and distribution underground to plant soil for enhancing plant growth is proposed. Iceland patent IS 2300, Shulenberger et al., presents a process which combines industrially captured $CO_2$ with $H_2$ from renewable energy driven electrolysis for the production of methanol by means of a low pressure and temperature process. PCT/IT2008/000559, submitted by A.S.T. Engineering s.r.l., presents a system closely modeled on the Carnol Process in which the $CO_2$ from industrial flue gas is separated from other emission components and mixed with $H_2$ from natural gas for methanol production. US 2008/0319093 A1, submitted by George Olah, aims to use industrial $CO_2$, not necessarily from industrial exit stacks, along with methane or natural gas for the production of methanol and methanol byproducts using "bi-reformation", a combination of steam reformation and dry reformation. PCT/BE2003/000016, submitted by Félicien Absil, discusses a method for the recovery of $CO_2$ from industries like cement plants or coal fired power stations for the production of syngas for heat energy and carbon nanotube production. US2008/0072496 A1 submitted by A. Yogev et al. relates to the thermochemical capture of $CO_2$ from gas by reaction with $K_2CO_3$ and producing methane or methanol fuel by releasing the captured $CO_2$ and reacting it with hydrogen. Commercial application of these processes is yet to be seen. It is to be noted that in most CCS or $CO_2$ reuse systems, the cost of $CO_2$ capture could be the largest cost component. A number of systems for the removal and recovery of $CO_2$ are described by Halmann et al. including, amine absorption, oxy-combustion, potassium carbonate absorption, molecular sieves, refrigeration, seawater absorption, pressurized, fluidized bed combustor, and membrane separation. On this topic, it is noted that both thermal and electrical energy are needed to remove and recover $CO_2$. PCT/EP2009/050205, PCT/EP2008/068212, PCT/US2008/084463, and PCT/US2008/084457, submitted by Alstom Technology, describe methods for the capture of $CO_2$ either through compressive means, solid materials or specialty systems. PCT/US2008/081998, submitted by Powerspan Corporation, describes a system in which a synergistic system removes $CO_2$ from a flue gas. WO 2008137815 A1 submitted by Clark describes a process where biomass feedstock is converted to synthesis gas streams where one is converted to $CO_2$ and steam for producing electricity and another is converted to fuel in a Fischer-Tropsch reactor. US2008/0303348A1 submitted by Witters describes a process for continuously generating baseload electrical energy from renewable resources utilizing biomass in boilers and capturing $CO_2$ to produce algae fuel.

Biomass utilization is a natural cycle of $CO_2$ capture and reuse. Biomass provides a potentially $CO_2$-neutral source of energy as the $CO_2$ released during processing and combustion is taken up by the next crop. Biomass is majorly used for transport fuel production through biochemical (fermentation, transesterification, and anaerobic digestion) or thermochemical (gasification, pyrolysis and conversion) methods. At present, the main transportation fuel available from biomass is ethanol. Haroon et al. studies that current ethanol production techniques from fermentation consume fossil carbon for energy and chemical inputs and it is these fossil carbon inputs that result in positive full-fuel-cycle emissions. Each liter of ethanol saves 1.85 kg of $CO_2$ by replacing gasoline, but at the same time releases 1.39 kg of $CO_2$ as produced in the US and 0.24 kg of $CO_2$ in Brazil. Thus the full-fuel-cycle analysis shows that current ethanol fuel systems are only partially successful at recycling $CO_2$ and being $CO_2$-neutral sources of energy. Full-fuel-cycle $CO_2$ emissions from corn ethanol in the USA nearly wipe out all of the $CO_2$ advantage of replacing gasoline. Another disadvantage of this process is that only a fraction of the biomass is converted to the final desired liquid fuels. This problem is also associated with proposed biofuel production from algae, which is currently un-economical and will likely remain so for the foreseeable future due to fundamental thermodynamic constraints (Krassen Dimitrov, 2007 Case Study). Thermochemical production pathways of biofuels from biomass could use biomass with higher efficiency. This process happens through an intermediate called synthesis gas, also known as syngas, which consists of a variable ratio mixture of $H_2$, CO, and $CO_2$. The conventional thermochemical process for liquid fuel production from biomass is presented in FIG. 1. Depending on the type of biomass and the conditions of syngas production, $CO_2$ concentration of the raw syngas output may vary from 6 to 40 mol % on dry basis. To obtain the required ratio of $CO/H_2$, water gas shift reaction is employed in which CO is reacted with $H_2O$ to generate more hydrogen thus releasing further $CO_2$. For example, methanol production processes from biomass produce around 600 to 1200 pounds of $CO_2$ per ton of methanol. The Hynol Process is employed for the conversion of carbonaceous materials into methanol via a syngas intermediate. Steam reformation and hydrogasification are performed in parallel in this system, and high conversion efficiency to the production of methanol is achieved. The Hynol Process causes a reduction of $CO_2$ emissions on the order of 30% relative to conventional processes for methanol production, but still causes the emission of approximately 103 pounds of $CO_2$ for each MMBTu of methanol produced (Halmann 249). U.S. Pat. No. 6,736,955B2 by Shaw, US2008/0115415A1 by Agrawal et al., US1995/5416245 by MacGroger et al. further overcome the problem of excess $CO_2$ generation by offsetting the stoichiometric imbalance of syngas with $H_2$ produced from off peak electricity. While Shaw and Agrawal et al. uses Reverse Water Gas Shift (RWGS) to reduce $CO_2$, MacGroger et al. plans to dissociate $CO_2$ to CO with energy generated from a Partial Oxidation (PDX) reactor to reduce $CO_2$. All the three methods use partial oxidation reactor or gasification system for syngas production either to produce methanol or any other liquid synthetic fuels. FIG. 2 depicts these modifications to the conventional prior art in addition to stable electrical power generation from hydrogen and syngas, proposed by Boyapati et al US2004/0265158A1. The success of the above processes to solve the problem of internal $CO_2$ generation and release is dependent on the availability, adaptability and effective utilization of carbon free energy sources for $H_2$ production, which has its own limitations as discussed previously.

SUMMARY OF THE INVENTION

The present disclosure provides a method and system to solve the previously described problems of increased $CO_2$ emissions, depleting fossil fuel sources and efficient storage and utilization of intermittent renewable energy. The method involves storing renewable energy in the form of renewable fuels or renewable chemicals or both and further integrated with the recycling and disposal of $CO_2$.

Accordingly, the present invention provides a method and system:
- To produce non-intermittent renewable electricity from intermittent renewable energy sources in conjunction with the utilization of gaseous fuel derived from carbonaceous feedstock.
- To produce or utilize renewable thermal energy from said renewable energy sources for internal process use.
- To produce an oxygen stream in an Oxygen Production Unit (OPU) utilizing at least a part of the said stable electricity produced.
- Utilizing at least a part of the said non-intermittent renewable electricity and oxygen, along with renewable carbonaceous feedstock and concentrated $CO/CO_2$ emissions to produce gaseous intermediates and gaseous fuel in a Gas Production Unit (GPU).
- To produce a hydrogen stream in a Hydrogen Production Unit (HPU) utilizing at least a part of said non-intermittent electricity produced and utilizing at least a part of said hydrogen in a GPU when renewable carbonaceous feedstock is considered deficient in hydrogen for producing suitable gaseous intermediates and fuels.
- To convert the chemical energy of the gaseous intermediates to more desirable fuels and chemicals in a Gas Conversion and Processing Unit (GCPU) where gas to liquid conversion technologies are used to produce valuable and easily transportable renewable fuels or renewable chemicals or both from the said gaseous intermediates.

In addition, the present invention also provides a method:
- To effectively capture $CO_2$ from fuel combustion emissions by enriching air for fuel combustion with said oxygen to obtain a concentrated $CO_2$ emission stream.
- To recycle at least a part of the said concentrated $CO_2$ emission stream to a GPU or a GCPU and converting it to renewable fuels or renewable chemicals or both.
- To dispose or re-use at least a part of the said concentrated $CO_2$ emission stream by any of available sequestering, storage or reuse techniques, either internal or external to the aforementioned method.

BRIEF DESCRIPTION OF THE DRAWINGS

The current invention addresses renewable energy storage and $CO_2$ capture, reuse and disposal. These and other advantages of the present disclosure may be more completely fully understood by means of the following description of the accompanying drawings of the prior arts and preferred embodiments of the invention in which.

DETAILED DESCRIPTION OF THE INVENTION

Figure 1:
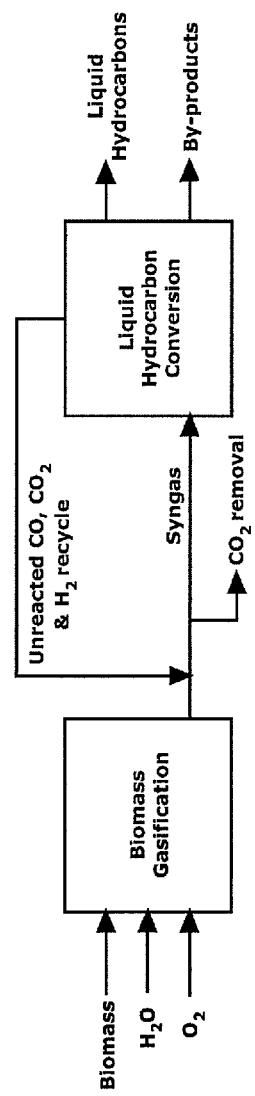
FIG. 1 is a Prior Arts schematic showing the conventional process for producing liquid fuels from biomass.
Figure 2:
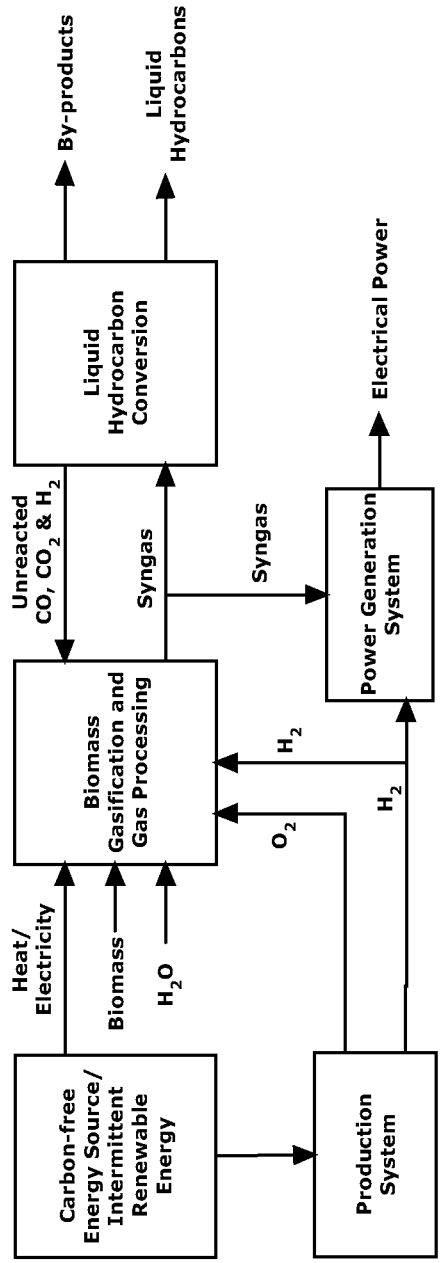
FIG. 2 is a Prior Arts schematic showing a process for producing liquid fuels using carbon free or intermittent renewable energy, recycling $CO_2$ and generating non-intermittent electrical power from hydrogen and syngas.
Figure 3:
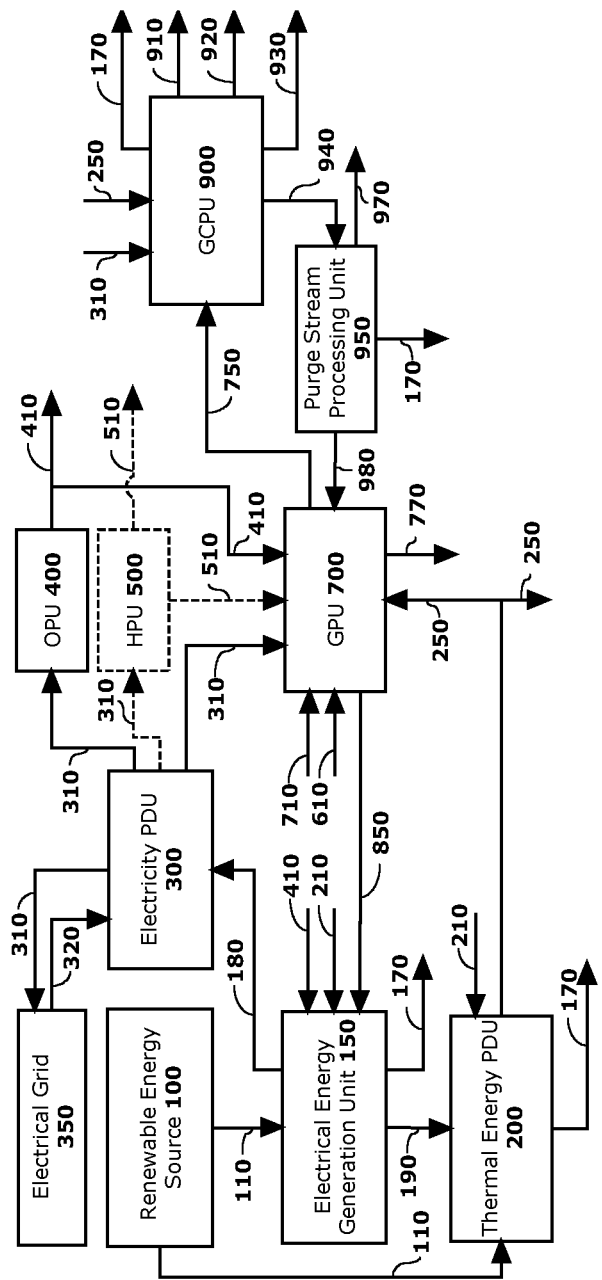
FIG. 3 is a schematic showing a method and system for converting renewable energy and renewable carbonaceous feedstock to non-intermittent renewable electricity and storing it as renewable fuels and renewable chemicals.

FIG. 3 shows a schematic diagram in relation to the method and system of the invention, of renewable energy utilization and storage through the production of non-intermittent electricity and conversion to fuels and chemicals. An intermittent renewable energy source 100 is typically characterized by its variability. Electricity production from these types of sources can be dynamic and/or intermittent depending on their nature and at times not stable enough for utilization by downstream processes. A person having ordinary skill in the art will understand the term intermittent as disclosed in the present invention. Gaseous fuel can be utilized in tandem to compensate for such variability due to its fast response and rise times in electrical power production.

A non-intermittent energy source is an energy source with substantially stable output, which is not dependent on intermittent conditions such as wind, sunshine, and the like. Non-intermittent renewable electricity 180, with a variability that is acceptable by the processes downstream can be achieved through co-generation of electricity from at least a part of fuel from the gaseous fuel stream 850, preferably produced from renewable carbonaceous feedstock 710 along with at least a part of the renewable energy 110 from the renewable energy source 100 in the electrical energy generation unit 150. At least a part of oxygen from the oxygen stream 410 is utilized instead of air for the generation of electricity from the gaseous fuel stream 850. The replacement of air with oxygen leads to a reduction in harmful $NO_x$ emissions and to the production of a concentrated $CO/CO_2$ emission stream 170 that can be sent for recycling or disposal.

At least a part of the non-intermittent renewable electricity 180 being generated is sent to an Electricity Processing and Distribution Unit (Electricity PDU) 300 where it is processed to meet the required specifications of various distribution points, viz. various internal processes and/or an external electrical grid 350, to become processed non-intermittent renewable electricity 310.

At least a part of the processed non-intermittent renewable electricity 310 from the Electricity PDU 300 is used to produce an oxygen stream 410 by an Oxygen Production Unit (OPU) 400.

Processed renewable thermal energy 250 is produced either from at least a part of the gaseous fuel stream 850, preferably produced from renewable carbonaceous feedstock 710 and/or from at least a part of the renewable energy 110 in the Thermal energy Processing and Distribution unit (thermal energy PDU) 200. At least a part of oxygen from the oxygen stream 410 is utilized instead of air for the generation of thermal energy from the gaseous fuel stream 850. The replacement of air with oxygen leads to a reduction in harmful $NO_x$ emissions and to production of a concentrated $CO/CO_2$ emission stream 170 that can be sent for recycling or disposal.

Preferably, at least a part of the renewable thermal energy 190 from the thermal energy PDU processing and distribution unit 200 and at least a part of the internal process heat 210 is sent to the electrical energy generation unit 150 where it can be utilized for non-intermittent renewable electricity production 180.

At least a part of: processed non-intermittent renewable electricity 310, processed renewable thermal energy 250, oxygen from the oxygen stream 410, concentrated $CO/CO_2$ recycling stream 610 and renewable carbonaceous feedstock 710 are utilized by a Gas Production Unit (GPU) 700 to produce a gaseous fuel stream 850, gaseous intermediate stream 750 and Process Waste Stream (PWS) 770. This gaseous fuel stream 850, from the GPU supports the production of non-intermittent renewable electricity 180 from the electrical energy generation unit 150. Thus, renewable carbonaceous feedstock 710 is effectively utilized to obtain non-intermittent renewable electricity 180 from sources of renewable energy 110.

At least a part of the gaseous intermediate stream 750 is converted to a renewable fuel stream 910, a renewable chemical stream 920 and a purge stream 940 in a Gas Conversion and Processing Unit (GCPU) 900. The GCPU 900 may also produce a Process Waste Stream (PWS) 930. Renewable carbonaceous feedstock thus acts both as a source of renewable energy for the non-intermittent renewable electricity production and as a source of materials for the conversion and storage of said electricity to renewable fuels and chemicals.

Preferably, at least a part of the purge gases from the purge stream 940 is further sent to a purge stream processing unit 950 to produce recyclable or combustible gas stream 980, at least a part of which is sent back to the GPU 700. The purge stream processing unit 950 also produces a purge waste stream 970 which can be sent for disposal.

A person having ordinary skill in the art will understand the term renewable as disclosed in the present invention. Preferably, the term renewable as used in the present disclosure, is applied to any material, gaseous, solid or liquid and energy that can be replaced by natural processes at a rate comparable or faster than its rate of consumption by human activities.

In some embodiments processes in the GPU 700 and/or the GCPU 900 emit concentrated $CO/CO_2$ streams. All such streams including the concentrated $CO/CO_2$ streams 170 from the electrical energy generation unit 150 and the thermal energy PDU 200 constitute internal emission sources of $CO/CO_2$ and can form at least a part of concentrated $CO/CO_2$ recycling stream 610. The source of carbon for these emissions is renewable carbonaceous feedstock. The renewable carbonaceous feedstock is either naturally replenished through absorption of atmospheric $CO_2$ or independently causes $CO_2$ release due to external circumstances, for example incineration of waste. Thus all the embodiments of the present invention are at least carbon neutral i.e. not emitting any positive $CO_2$ emissions during the system operation, without considering any $CO_2$ emissions from the renewable energy source 100. Some embodiments of the present invention are carbon negative i.e. they can take in extra $CO_2$ emissions and recycle in the form of renewable chemicals when excess hydrogen is available such as when renewable energy output is high from intermittent renewable energy sources or when renewable carbonaceous feedstock contains high amounts of hydrogen.

Renewable sources of energy 100 include, but are not limited to wind, geothermal, solar, aerothermal, hydroelectric, biomass, tidal, OTEC, osmosis, off peak energy and renewable steam. In some embodiments of the invention, renewable sources of energy can include stranded sources of energy. A person having ordinary skill in the art will understand the term "stranded sources of energy" as disclosed in the present invention. Preferably, the term "stranded sources of energy" as used in the present disclosure refers to any available energy due to mismatch to the end user's demand or where the direct supply of energy to the end user is technically or economically unfeasible. This can be due to the unavailability or shortcomings in energy storage and distribution infrastructure.

The electrical energy generation unit 150 converts at least a part of the renewable energy 110 from the renewable energy source 100, at least a part of fuel from the gaseous fuel stream 850 and oxygen from the oxygen stream 410 to non-intermittent renewable electricity 180 through any one of or a combination of commercially available methods including but not limited to: conversion of mechanical, thermal, gravitational, nuclear, photonic, chemical or biological energy to non-intermittent renewable electricity.

In some embodiments of the invention, the renewable energy source 100 such as but not limited to wind, solar, tidal and osmosis have intermittent or varying renewable energy 110 output. Such variation in the renewable energy 110 is compensated by energy from at least a part of fuel from the gaseous fuel stream 850 to produce non-intermittent renewable electricity 180 from the electrical energy generation unit 150.

In some embodiments of the invention, variable electricity is produced internal to the electrical energy generation unit 150 from the renewable energy 110 which is variable. This variable electricity is stabilized using the electricity generated from at least a part of fuel from the gaseous fuel stream 850 internal to the electrical energy generation unit 150. Preferably, electricity generation from at least a part of fuel from the gaseous fuel stream 850 can be achieved through any available means including but not limited to one of or combination of the following technologies: gas turbine air combustion, gas turbine oxy-rich combustion, gas fired steam turbine, combined cycle gas turbine and hydrocarbon fuel cells.

In some embodiments of the invention the variability of the renewable energy 110 is compensated for by the energy released from at least a part of fuel from the gaseous fuel stream 850 to produce non-intermittent renewable energy. This non-intermittent renewable energy is used to generate non-intermittent renewable electricity 180 in the electrical energy generation unit 150.

In some embodiments of the invention, the gaseous fuel stream 850 consists preferably of fuels in gaseous form due to their faster response times in energy release as compared to liquid and solid forms of fuel.

In some embodiments of the invention, at least a part of renewable fuel from the renewable fuel stream 910 can form at least a part of the gaseous fuel stream 850.

Preferably, in some embodiments of the invention, at least a part of the fuel from the gaseous fuel stream 850 can be stored before use to act as temporary energy storage and buffer to the electrical energy generation unit 150.

In some embodiments of the invention, the electrical energy generation unit 150 can comprise of one or more individual electricity production units, where independent electricity production from the available resources takes place.

Preferably, in some embodiments of the invention, individual electricity production units can generate electricity from at least a part of fuel from the gaseous fuel stream 850 and/or oxygen from the oxygen stream 410 in combination with other available methods for energy storage including, but not limited to: Compressed Air Energy Storage (CAES), Pumped Storage Hydropower (PSH) and Thermal Energy Storage (TES). In one embodiment of the invention, wind energy is captured as mechanical energy and effectively stored as compressed air. At least a part of the stored energy in the form of compressed air is then released on demand through combustion with at least a part of gaseous fuel from the gaseous fuel stream 850. In another embodiment of the invention, at least a part of the chemical energy of the fuel in the gaseous fuel stream 850 is converted to thermal energy through combustion and stored for subsequent release using any commercially available means of storing and converting thermal energy to electricity.

In some embodiments of the invention, variations in the renewable energy 110 from the renewable energy source 100 take place over longer timescales (days as opposed to minutes) and can be predicted with sufficient accuracy to allow for generation of non-intermittent electricity by combining them with other forms of electricity generation from renewable energy (other than from gaseous fuel stream). This can include but is not limited to co-generation of electricity from: the renewable fuel stream 910; complementary intermittent or controllable non-intermittent renewable energy sources. These complementary intermittent or controllable non-intermittent sources of renewable energy include but are not limited to: tidal, solar, wind and osmosis electricity generation. In one embodiment of the invention, a decrease in renewable energy output from solar thermal power during nighttime is compensated for with thermal energy generation from combustion of at least a part of fuel from the gaseous fuel stream 850.

In some embodiments of the invention, the gaseous fuel stream 850 can be utilized to meet any additional demand for non-intermittent renewable electricity.

The electricity processing and distribution unit 300 receives non-intermittent renewable electricity 180 for processing and final distribution of the processed non-intermittent renewable electricity 310 to internal process units and external grid. The electricity processing and distribution unit 300 can comprise of one or several individual processing and/or distribution units including but not limited to: distribution substations, transmission substations, transformers, rectifiers and inverters where the amplitude and phase of voltage and current of incoming electricity is transformed to meet specifications and supplied to various process units as necessary.

In some embodiments of the invention, the electricity processing and distribution unit 300 can temporarily store the non-intermittent renewable electricity 180 it receives before processing and/or store the processed non-intermittent renewable electricity 310 after it is produced and until it is used. Such temporary storage can be in any available form including but not limited to battery storage, capacitor and supercapacitor storage or superconducting magnetic storage.

The term "processed non-intermittent electricity" as used in the present disclosure is applied to any electrical power whose output varies minimally such as not to affect the internal process units and or fuel or chemical production capacities. More specifically, variations in electrical output are kept within the range where processing and production units are able to respond on the same timescale to minimize the effects on the production process.

In some embodiments of the invention, at least a part of the processed non-intermittent renewable electricity 310 can be supplied to an external electrical grid 350, preferably to replace electrical power production from fossil fuels.

In some embodiments of the invention, the renewable grid electricity 320 can be supplied to the system from an existing electrical grid if the grid electricity source is primarily renewable.

In some embodiments of the invention, the OPU 400 is one or a combination of electrolysis of water and Air Separating Unit (ASU). Preferably, in some embodiments, ASU can comprise of any commercially available oxygen production system from air, such as Cryogenic Air Separation (CAS) or Vacuum Pressure Swing Adsorption (VPSA).

In some embodiments of the invention, a part of the processed non-intermittent renewable electricity 310 from the Electricity PDU 300 is used to produce a hydrogen stream 510 by a Hydrogen Production Unit (HPU) 500. In some embodiments of the invention when renewable carbonaceous feedstock 710 is considered deficient in hydrogen content, a part of said hydrogen from the hydrogen stream is utilized by a Gas Production Unit (GPU) 700 to produce a gaseous fuel stream 850, gaseous intermediate stream 750 and Process Waste Stream (PWS) 770.

In some embodiments of the invention, the production of the hydrogen stream 510 by a HPU 500 is achieved by at least one of or a combination of: electrolysis of water, dehydrogenation of renewable hydrocarbons, biological hydrogen production, chemical hydrogen production, photochemical hydrogen production, thermo-chemical hydrogen production and any other production method of renewable hydrogen.

In some embodiments of the invention, at least a part of hydrogen from the hydrogen stream 510 and oxygen from the oxygen stream 410 are temporarily stored in either gaseous or liquid or chemical form separately before use. Preferably, the hydrogen stream 510 and the oxygen stream 410 have a purity of at least 90% by volume on a dry basis of hydrogen and oxygen respectively. More preferably, hydrogen stream should have a purity of at least 95% by volume of hydrogen on a dry basis. More preferably, Oxygen stream should have a purity of at least 95% by volume of oxygen on a dry basis. In some embodiments, some or all of the hydrogen and oxygen streams can be considered commercial value products.

In some embodiments of the invention, the oxygen and hydrogen are stored temporarily in the OPU 400 and the HPU 500 respectively before forming the oxygen stream 410 and the hydrogen stream 510 respectively.

In some embodiments of the invention, at least a part of the oxygen from the oxygen stream 410 is used for various internal processes for combustion and gasification.

In some embodiments of the invention, some or all the oxygen from the oxygen stream 410 that is not required for internal processes is supplied to external combustion processes to enrich air for fuel combustion (oxy-combustion/oxy-firing/oxy-fuel combustion), whereby a concentrated $CO/CO_2$ emission stream is produced.

In some embodiments of the invention, a HPU 500 can also simultaneously function as an OPU 400 and vice versa. For example hydro-splitting system producing the hydrogen stream 510 through the dissociation of water also produces an oxygen stream 410, thus acting simultaneously as both a HPU 500 and an OPU 400.

In some embodiments of the invention, at least a part of oxygen from the oxygen stream 410 is considered a valuable by-product of the process, because the process produces more oxygen than the requirement for internal process consumption. For example, in one embodiment where both the oxygen stream 410 and the hydrogen stream 510 are produced by water electrolysis there is a possibility that all the hydrogen from the hydrogen stream 510 is consumed in the internal process while only a part of the oxygen from the oxygen stream 410 is utilized. This excess oxygen is thus a valuable by-product for example its utilization in oxy-fuel combustion has an added economical benefit and does not require to have a separate production of oxygen.

In some embodiments of the invention, the process utilizes less hydrogen than is produced and thus at least a part of hydrogen from the hydrogen stream 510 is considered a valuable by-product of the process.

At least a part of oxygen from the oxygen stream 410 is used to gasify the renewable carbonaceous feedstock 710 in a Gas Production Unit (GPU) 700. Oxygen, instead of air, is used for such gasification in order to produce output gaseous streams with low $N_2$ concentrations, preferably less than 10% and more preferably less than 5%. This reduces $N_2$, an inert to the downstream processes, which only increases the power consumption and a can cause losses of part of the valuable synthesis gases produced in the process.

The term "renewable carbonaceous feedstock", as used in the present disclosure, is applied to any material, gaseous, solid or liquid that has sufficient carbon content and can be replaced by natural processes at a rate comparable or faster than its rate of consumption by human activities. The term "sufficient carbon content" is applied to any material that is rich in carbon such that carbon comprises preferably at least 5% of the material by weight. Renewable carbonaceous feedstock may also refer to some waste materials and chemicals that would otherwise require disposal. Renewable carbonaceous feedstock include, but are not limited to: timber harvesting residues, soft-wood chips, tree branches, tree stumps, leaves, bark, sawdust, paper pulp, corn stover, wheat straw, switch grass, rice straw, sugarcane bagasse, miscanthus, animal manure, municipal solid waste, municipal sewage, commercial waste, used tires, grape pumice, almond shells, pecan shells, coconut shells, coffee grounds, grass pellets, hay pellets, card board, paper, plastic, rubber, glycerol, black liquor, cloth, lignin, waste oil, biogas, carbon dioxide, carbon monoxide and any combinations thereof.

In some embodiments of the invention, the term Gas Production Unit (GPU) refers to a combination of Carbonaceous Processing Units (CPUs) and Individual Production Units (IPUs).

The term Carbonaceous Processing Unit (CPU) as used in the present disclosure is applied to any system that modifies the physical characteristics of the renewable carbonaceous feedstock 710. Such modification facilitates the use of renewable carbonaceous feedstock 710 in the GPU 700 with ease and efficiency. In some embodiments of the invention, the term Carbonaceous Processing Unit (CPU) refers to any commercially available method including but not limited to one of or a combination of: drying, grinding, cutting, torrefaction, crushing, heating or mixing of the renewable carbonaceous feedstock 710.

In some embodiments of the invention, the Individual Production Unit (IPU) comprises of a reactor to carry out chemical reactions including but not limited to the reactions of one of or a combination of devolatilization, hydrogasification, pyrolysis, partial oxidation, steam reformation, dry reformation, anaerobic digestion and the reversible water gas shift reaction to produce gaseous streams for downstream processes.

In some embodiments of the invention, syngas is produced from the gasification of biomass ($CH_xO_y$). An overall simplified reaction describing gasification of biomass using steam and oxygen is given by:

$$CH_xO_y + O_2 + H_2O \text{ (steam)} \rightarrow CH_4 + CO_2 + CO + H_2 + H_2O \text{ (unreacted steam)} + char + tar \quad (1)$$

After biomass processing, common steps involved in the gasification process are described by the following reactions:

$$2C + O_2 \rightarrow 2CO \text{ (partial oxidation reaction)} \quad (2)$$

$$C + O_2 \rightarrow CO_2 \text{ (complete oxidation reaction)} \quad (3)$$

$$C + H_2O \rightarrow CO + H_2 \text{ (water gas reaction)} \quad (4)$$

$$C + 2H_2 \rightarrow CH_4 \text{ (hydrogasification reaction)} \quad (5)$$

$$CO_2 + H_2 \rightarrow CO + H_2O \text{ (water gas shift reaction)} \quad (6)$$

$$CH_4 + H_2O \rightarrow CO + 3H_2 \text{ (steam reforming reaction)} \quad (7)$$

$$C + CO_2 \rightarrow 2CO \text{ (Boudouard reaction)} \quad (8)$$

The IPUs typically convert the renewable carbonaceous feedstock 710 to a gaseous intermediate stream 750, a gaseous fuel stream 850 and a process waste stream 770. The choice of reaction for an IPU affects the energy content of the product gas. In some embodiments of the invention, the type of reactor in an IPU can include but is not limited to a fixed-bed or fluidized bed reactors.

In some embodiments of the invention, the term "gaseous intermediate" refers to gaseous feedstock that can be produced from the available renewable carbonaceous feedstock and converted to any form of a renewable fuel stream 910 and/or a renewable chemical stream 920 by a Gas Conversion and Processing Unit (GCPU) 900. Preferably, in some embodiments, the gaseous intermediate stream 750 comprises of at least 90% by volume of one of or a combination of syngas, at least a part of hydrogen from the hydrogen stream 510 and methane; and a total hydrogen content of at least 10% by volume and preferably 30% by volume.

A person having ordinary skill in the art will understand the terms "syngas" or "synthesis gas" as disclosed in the present invention. Preferably, the term "syngas" or "synthesis gas", as used in the present disclosure is a gas mixture containing $CO/H_2/CO_2$ in any molar ratio, with all the three gases together accounting to a volume greater than 60% of the gas mixture.

In some embodiments of the invention, the term "biogas" refers to any gas produced by the biological breakdown of organic matter in the absence of oxygen (anaerobic digestion or fermentation). A simplified chemical equation for the overall processes is as follows:

$$C_6H_{12}O_6 \rightarrow 3CO_2 + 3CH_4 \quad (9)$$

Preferably, biogas is a gas mixture containing $CH_4$ and $CO_2$ in any ratio that accounts for a volume greater than 60% of the gas mixture. Sources of biogas include, but are not limited to: swamp gas, marsh gas, landfill gas and digester gas.

In another example syngas can be produced from methane rich biogas from any one of or a combination of steam reforming (eq. 10), partial oxidation (eq. 11) or dry reforming (eq. 12).

$$CH_4 + H_2O \rightarrow CO + 3H_2 \quad (10)$$

$$CH_4 + \tfrac{1}{2}O_2 \rightarrow CO + 2H_2 \quad (11)$$

$$CH_4 + CO_2 \rightarrow 2CO + 2H_2 \quad (12)$$

Preferably, raw syngas of a specific ratio of $CO/CO_2/H_2$ may be produced from each IPU and may be combined with syngas from one or more IPUs to produce various raw syngas mixtures of any desired ratios of $CO/CO_2/H_2$. Any required adjustments to the syngas mixture can be achieved through increased or decreased addition of at least a part of hydrogen from the hydrogen stream 510, at least a part of $CO/CO_2$ from the concentrated $CO/CO_2$ recycling stream 610 and through adjustments of gasification conditions, throughput and feedstock. In some embodiments adjustments to the output syngas stream can alternatively be achieved through various chemical reactions including but not limited to: the reversible Water Gas Shift Reaction (WGSR) (eq. 6), the Boudouard reaction (eq. 8), dry reforming (eq. 12) and electrochemical reduction (eq. 13).

$$CO_2 + e^- \rightarrow CO + \tfrac{1}{2}O_2 \quad (13)$$

The resulting concentration and composition of $CO$, $H_2$, $CH_4$, $CO_2$ and $H_2O$ in the exhaust from gasification of the carbonaceous feedstock in the IPUs varies according to the quantity of oxidant, composition of the carbonaceous feedstock, steam fed to the gasifier, gasifier type, reaction conditions viz. pressure and temperature. Thus gas mixtures with various ratios could be produced to meet the needs of the GCPU 900 for producing various renewable fuel streams 910 and chemical streams 920. In some embodiments of the invention, addition of hydrogen from the HPU and or concentrated $CO/CO_2$ is necessary to ensure optimal syngas composition for complete utilization of available feedstock.

In some embodiments of the invention the GPU 700 comprises of gas purification units to purify at least a part of the gaseous intermediate stream 750 and/or the gaseous fuel stream 850. Gas purification includes but is not limited to removal of chemicals which are either poisonous to the downstream processes and/or are make the desired products off-specification. Preferably, gas purification units employ any one of or combination of the following methods including but not limited to: physical and chemical adsorption; absorption, gas membrane separation, cryogenic separation and chemical conversion. Preferably gas purification unit can comprise of any one or a combination of commercially available technology for purification of gases, including but not limited to: Rectisol and Selexol for sulphur removal, alkanolamine scrubbing and the Claus process. Preferably, the purification of the raw syngas mixtures may be employed prior to feeding of the gas to the GCPU 900 or the electrical energy generation unit 150.

In some embodiments of the invention, any process waste 770 including but not limited to ash, char, tar, elemental sulfur, metals and inert gases produced by the processing, gasification and purification of renewable carbonaceous feedstock 710 is sent for further treatment and disposal as is required.

Preferably, the combination of IPUs and CPUs can be parallel or in series or both, where mass, energy and information exchange may be possible. Preferably, material fed to the GPU 700, may be divided among various IPUs as per requirements.

In some embodiments of the invention, the method further comprises of a method of adjusting the amount of oxygen from the oxygen stream 410 to the renewable carbonaceous feedstock 710 as input to the GPU 700 such that the final gaseous intermediate stream contains oxygen less than 2% by volume, more preferably free of oxygen. In some embodiments of the invention, the adjustment of the oxygen could be to a level, where there is some ungasified feedstock, not more than 5% by weight of input feedstock.

In some embodiments of the invention, at least a part of the fuel from the gaseous fuel stream 850 is stored temporarily as a part of the GPU 700.

In some embodiments of the invention, at least a part of the gas from the gaseous intermediate stream 750 is stored temporarily as a part of the GPU 700.

In some embodiments of the invention, the internal processes in the GPU 700 and the GCPU 900 require thermal energy and electricity. This electricity is supplied by the Electricity PDU 300. The thermal energy is supplied by the Thermal energy Processing and Distribution Unit (Thermal energy PDU) 200 as processed renewable thermal energy 250 in a form to be distributed among the required processes. The thermal energy PDU 200 uses one or a combination of at least a part of renewable energy 110 directly from the renewable energy source 100 such as geothermal or solar thermal energy or at least a part of thermal energy from the internal process heat 210 or at least a part of the renewable thermal energy 190 which is any thermal energy produced as part of electrical energy generation unit. The term internal process heat 210 as used in the present disclosure refers to the thermal energy produced internal to the system including but not limited to any one of or a combination of exothermic reactions, cooling of flow streams and combustion of internally produced gaseous or liquid fuels.

In some embodiments of the invention, at least a part of thermal energy from the internal process heat 210 and at least a part of the renewable thermal energy 190 is supplied directly to internal processes.

In some embodiments of the invention, at least a part of thermal energy from the internal process heat 210 is used to produce at least a part of the non-intermittent renewable electricity 180 in the electrical energy generation unit 150.

Gaseous intermediate stream 750, processed non-intermittent renewable electricity 310 and processed renewable thermal energy 250 are supplied to a Gaseous Conversion and Processing Unit (GCPU) 900 where a renewable hydrocarbon fuel stream 910, a renewable chemical stream 920 and a process waste stream 930 are produced. The GCPU 900 is a hydrocarbon fuel and chemical production unit typically comprising of any number of Internal Gas Conversion Units (IGCU) such as a Syngas Conversion Unit (SCU) or a Biogas Conversion Unit (BCU) where gas to chemical or fuel synthesis is performed, for example Fischer Tropsch synthesis.

The term Internal Gas Conversion Unit as used in the present disclosure is applied to a unit that comprises of a reactor that is commercially available to carry out the conversion of at least a part of gases from the gaseous intermediate stream 750 such as the syngas or biogas to form the renewable fuels stream 910 or the renewable chemicals stream 920 or both. These reactors employ methods that include but are not limited to: thermochemical, electrochemical, biochemical and biological methods for the conversion of gaseous intermediates to hydrocarbons, carbohydrates, alcohols and ethers including but not limited to: methanol, ethanol, higher alcohols, sugars, dimethyl ether, diesel and other saturated or unsaturated hydrocarbons that can be utilized as fuels or synthesis chemicals.

For example, a well established thermochemical method for syngas conversion to liquid fuels is through Fischer-Tropsch synthesis (FT). FT reactors commonly operate in a temperature range from 150° C. to 375° C. and pressure range 1 to 100 bar using a metal catalyst such as iron, cobalt, nickel, copper, zinc, ruthenium and any combinations thereof: a metal oxide of the aforementioned metals and combinations thereof in addition to various promoters and support materials such as silica and alumina Fischer-Tropsch reactor preferably produces C10-C20 hydrocarbons from syngas. A simplified reaction scheme is as follows:

$$(2n+1)H_2 + nCO \rightarrow C_nH_{2n+2} + nH_2O \tag{14}$$

In another example, methanol fuel is produced from CO syngas (eq. 15) or from $CO_2$ syngas (eq. 16) using copper/zinc oxide based catalysts.

$$CO + 2H_2 \rightarrow CH_3OH \tag{15}$$

$$CO_2 + 3H_2 \rightarrow CH_3OH + H_2O \tag{16}$$

In some embodiments of the invention, the renewable fuel stream 910 and the renewable chemical stream 920 comprises of any one of or a combination of chemicals containing carbon, hydrogen and oxygen, including but not limited to: hydrocarbons, carbohydrates, alcohols and ethers such as: methanol, ethanol, higher alcohols, sugars, dimethyl ether, diesel and other saturated or unsaturated hydrocarbons that can be utilized as fuels or synthesis chemicals. In addition the renewable chemical stream 920 can comprise of any one or a combination of renewable chemicals including but not limited to: polymers, elastomers and plastics, pharmaceuticals and other industrial or fine chemicals of higher commercial value.

In some embodiments of the invention, the Gaseous Conversion and Processing Unit (GCPU) 900 performs internal conversion of at least a part of fuel from the renewable fuel stream 910 to form at least a part of chemicals of the renewable chemicals stream 920.

Preferably, in some embodiments of the invention, the renewable fuel stream comprises of desirable fuels produced through the conversion of less desirable chemicals from at least a part of the renewable chemical stream 920 and fuels from at least a part of the renewable fuel stream 910 in the GCPU 900. The term desirable fuels as used in the present disclosure refers to the fuels that can be directly utilized by the end user and or have higher commercial value. One example of this would be the conversion of crude methanol water mixture (eq. 16) to high octane gasoline as described by the Mobil Methanol-to-Gasoline (MTG) process where methanol is dehydrated and subsequently polymerized into alkanes over a zeolite catalyst. The MTG reactor can be a fluidized bed MTG reactor or a fixed bed MTG reactor or any alternative thereof.

In some embodiments of the invention, a purge stream 940 is produced from the GCPU 900 in order to reduce the build-up of the inert gases to the reactions in GCPU 900. Preferably, the purge stream 940 comprises of process inerts at least 50% by volume, more preferably 80% by volume.

The purge stream 940 is sent to a purge stream processing unit 950 where at least a part of $H_2$, CO, $CO_2$, $CH_4$ and other recyclable or combustible gases from the purge stream is recycled back into the GPU 700 as a recyclable or combustible gas stream 980. Purge stream processing typically involves separation of the gases, liquids or solids present in the purge stream 940. This can be achieved by various separation technologies including but not limited to: physical adsorption or absorption and release, chemical adsorption or absorption and release, cryogenic separation, membrane separation and distillation.

In some embodiments of the invention, the purge stream processing unit 950 produces a purge waste stream 970 which is sent for further treatment and disposal. The purge waste typically comprises of not only process inerts such as nitrogen but also some of the synthesis gases that cannot be separated and recycled economically. For example hydrogen from the purge stream 940 can be separated by using membrane separation technology and sent back to the GPU 700, any remaining hydrogen which could not be separated then forms a part of the purge waste stream 970.

Preferably, in some embodiments of the invention, at least a part of the recyclable or combustible gas stream 980 could form at least a part of the gaseous fuel stream 850.

Figure 4:
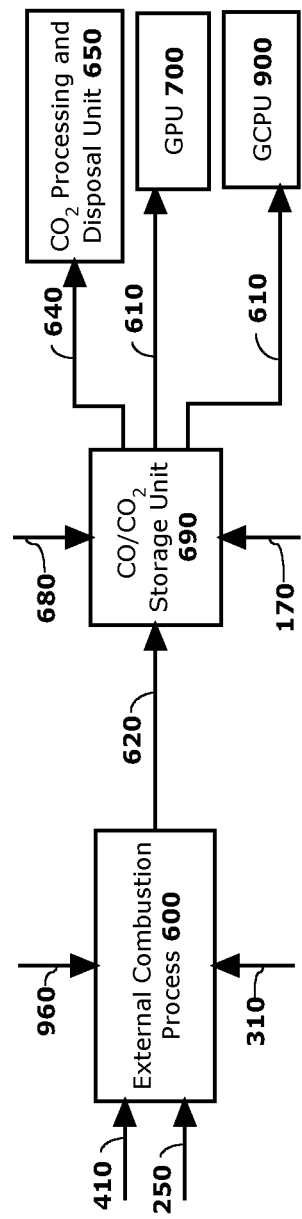
FIG. 4 is a schematic showing an additional method and system to the one shown in FIG. 3. where renewable energy is utilized to capture and recycle or dispose of $CO_2$ emissions from external combustion processes.

FIG. 4 shows a schematic diagram describing an addition to the method depicted in FIG. 3. In this preferred embodiment of the invention, at least a part of oxygen from the oxygen stream 410 and fuel from the combustion fuel stream 960 are supplied to the external combustion process unit 600 where oxy-rich combustion of the fuel takes place. This produces a higher concentrated $CO/CO_2$ stream 620 compared to air combustion.

Removal of the nitrogen component in the input air can reduce fuel consumption and heat loss due to heating of inert gases. Oxy-rich combustion produces approximately 75% less flue gas than air fueled combustion with the flue gas consisting primarily of $CO_2$ and $H_2O$. In some embodiments of the invention a part of the flue gas is recycled back into the oxygen stream to control the flame temperature. In addition, $NO_x$ emissions are decreased by the reduction or removal of $N_2$ in the combustion system. Therefore, possibly no $NO_x$ abatement systems are required in relevant combustion processes. Another possible benefit is low sizing of emission handling system as a result of the low amounts of $N_2$ present.

In some embodiments of the invention, combining at least a part of oxygen from the oxygen stream 410 and $CO/CO_2$ from the emission streams 170, 680, 620, 610, 640 produces a stream of substitute combustion air to be used in an external combustion processes unit 600. Substitute combustion air stream contains oxygen and $CO/CO_2$ in the appropriate ratios for replacing air with unmodified external combustion equipment to produce a concentrated $CO/CO_2$ stream 620.

The internal concentrated $CO/CO_2$ stream 170 is any one of or combination of: concentrated $CO/CO_2$ emission streams from the electrical energy generation unit 150; thermal energy PDU 200; GPU 700; GCPU 900; and purge stream processing unit 950.

In some embodiments of the invention, at least a part of $CO/CO_2$ from the $CO/CO_2$ stream 620 is sent to a $CO/CO_2$ storage unit 690 for temporary storage along with at least a part of the internal concentrated $CO/CO_2$ stream 170 and the external concentrated $CO/CO_2$ 680.

Preferably, at least a part of the $CO/CO_2$ in the $CO/CO_2$ storage unit 690 is sent as a concentrated $CO/CO_2$ recycling stream 610 to the GPU 700 and/or the GCPU 900 for possible recycling into a renewable fuel stream 910 and or renewable chemical stream 920. This recycling is possible when the required hydrogen is produced as a result of high amounts of renewable energy sources being available.

Preferably, at least a part of the $CO_2$ in the $CO/CO_2$ storage unit is sent as a concentrated $CO_2$ stream 640 to a $CO_2$ processing and disposal unit 650.

The above processes reduce $CO_2$ emission from external combustion and internal processes. Thus these preferred embodiments of the present invention are independently carbon negative i.e. absorbing $CO_2$ emissions during the process operation, without considering any $CO_2$ emissions from the renewable energy source 100. This is possible through the use of oxygen, a by-product of the process shown in FIG. 3.

In some embodiments of the invention, at least a part of the internal concentrated $CO/CO_2$ emission streams 170 and or external sources of concentrated $CO/CO_2$ streams 680 are sent directly to any of the GPU 700, the GCPU 900 and the $CO_2$ processing and disposal unit 650.

Preferably, the combustion fuel stream 960 is any gas, liquid or solid that can be combusted for energy generation, preferably renewable. In some embodiments of the invention, at least a part of the combustion fuel stream 960 comprises of at least a part of renewable fuel from the renewable fuel stream 910 and or at least a part of fuel from the renewable carbonaceous feedstock derived gaseous fuel stream 850.

In some embodiments, thermal energy generated from the oxy-rich fuel combustion of the combustion fuel stream 910 is considered as a source of internal process heat 210.

Preferably, the concentrated $CO/CO_2$ streams 170, 610, 620, 680 comprise of CO and $CO_2$ of at least 60% of the total stream volume. In some embodiments concentrated $CO/CO_2$ streams comprise of CO and $CO_2$ at least 80% of the total stream by volume.

Preferably, the external fuel combustion emissions and thus the concentrated $CO/CO_2$ stream 620 is obtained from industries that deploy fuel combustion in their processes which include but are not limited to: production of cement, aluminum, ferrosilicon, steel, pulp and electricity or co-generation through gasification of coal or natural gas.

External concentrated sources of $CO/CO_2$ 680 include, but are not limited to: geothermal power plants or natural springs, emissions from fermentation processes and the production of ammonia and ethylene oxide. Preferably, in some embodiments the $CO/CO_2$ storage unit 690 can include metallic carbonate storage, geological storage and any other forms of storage that can supply concentrated streams of $CO/CO_2$ in addition to conventional gas storage vessels.

Preferably, in some embodiments, a concentrated $CO_2$ stream 640 can be sent to a $CO_2$ processing and disposal unit 650. $CO_2$ disposal is achieved through any method of recycling/re-using or sequestering $CO_2$ that prevents its release into the atmosphere. More specifically, the $CO_2$ disposal method comprising the $CO_2$ disposal unit 650 includes but is not limited to one or a combination of the following: enhanced oil recovery (EOR), geo-sequestration, ocean storage and mineral storage. Disposal of a concentrated $CO_2$ stream 640 directly or indirectly coming from external oxy-fuel combustion processes becomes feasible since major costs associated with its disposal are due to the high cost of capturing $CO_2$. In the current disclosure carbon capture is effectively achieved through oxy-fuel combustion. In some embodiments, the re-use of clean fuel reduces the amount of sulfur and other impurities, thus further reducing the cost of $CO_2$ disposal. Preferably specifications for the composition of the $CO_2$ stream for EOR and sequestration can vary slightly, with $CO_2$ generally required as higher than 96% of the stream volume.

Preferably, the concentrated $CO/CO_2$ recycling stream 610 may contain other elements considered as inert to the system by up to 20% by volume. More preferably, the concentrated $CO/CO_2$ recycling stream 610 may contain other elements considered as inert to the system by up to 10% by volume. These inert compounds should not present any major problems, either to the production process or to the required quality of the final desired product.

Preferably, in some embodiments, purification of the concentrated $CO/CO_2$ streams for recycling 610 or the $CO_2$ stream for disposal 640 can be performed by separate purification units, preferably internal to the $CO/CO_2$ storage unit 690 prior to feeding in to the $CO_2$ processing and disposal unit 650 or GPU 700 or GCPU 900. Alternatively $CO/CO_2$ purification is achieved by internal purification units internal to the $CO_2$ processing and disposal unit 650 and GPU 700 or GCPU 900. Purification is performed to eliminate or separate any undesirable compounds from any of the further process steps and to meet the desired specifications of the end products. Preferably, the concentrated $CO/CO_2$ streams 170, 610, 620, 680 may contain carbon monoxide up to 90% of volume of the CO and $CO_2$ gas mixture. Preferably, in some embodiments the concentrated $CO/CO_2$ streams 170, 610, 620, 680 may contain inert compounds at most 3% of the purified streams. More preferably, in some of the embodiments the concentrated $CO/CO_2$ streams 170, 610, 620, 680 may contain inert compounds at most 1% of the purified streams.

Preferably, any commercially available $CO/CO_2$ purification system can be used for $CO/CO_2$ purification which employ any one of or a combination of various $CO/CO_2$ purification technologies including but not limited to: physical adsorption or absorption and release, chemical adsorption or absorption and release, cryogenic separation and membrane technologies.

We claim:

1. A method for storing renewable energy and recycling carbon oxides as renewable fuel, the method comprising:
    a. producing a gaseous fuel stream and a gaseous intermediates stream from a renewable carbonaceous feedstock and concentrated $CO/CO_2$ emissions;
    b. generating a non-intermittent renewable electricity from energy from at least one intermittent renewable source and at least a part of said gaseous fuel stream;
    c. producing an oxygen stream from at least a part of said non-intermittent renewable electricity;
    d. producing said gaseous fuel stream and said gaseous intermediates stream from at least a part of said oxygen stream, and
    e. producing a non-intermittent renewable fuel stream from at least a part of said gaseous intermediates stream.

2. The method of claim 1 further comprising producing at least one renewable chemical from at least a part of said gaseous intermediates stream.

3. The method of claim 1 further comprising producing a hydrogen stream from at least a part of said non-intermittent renewable electricity.

4. The method of claim 1 further comprising producing at least a part of said concentrated $CO/CO_2$ emissions from at least a part of said oxygen stream.

5. The method of claim 4 wherein at least a part of said concentrated $CO/CO_2$ emissions is disposed of to prevent $CO/CO_2$ release into the atmosphere.

6. The method of claim 1 wherein said concentrated $CO/CO_2$ emissions are selected from the group consisting of (a) concentrated $CO/CO_2$ emissions from oxygen rich fuel combustion processes wherein at least a part of said oxygen stream is utilized in said combustion; (b) concentrated $CO/CO_2$ emissions generated by at least one of production of said non-intermittent renewable electricity, production of said oxygen stream, production of said gaseous fuel stream, production of said gaseous intermediates stream, and production of said non-intermittent renewable fuel stream; and (c) concentrated $CO/CO_2$ emissions from an external source, wherein the external source comprises geothermal power plants, natural springs, fermentation processes, chemical production processes, industrial production processes, and combinations thereof.

7. The method of claim 1 wherein at least a part of said concentrated $CO/CO_2$ emissions is stored before use.

8. The method of claim 1 wherein a combined concentration of CO and $CO_2$ in said $CO/CO_2$ emissions is at least 30% by volume.

9. The method of claim 5 wherein the concentration of $CO_2$ in said $CO/CO_2$ emissions for disposal is at least 90% by volume.

10. The method of claim 5 wherein $CO_2$ is disposed by a method selected from the group consisting of sequestration underground or underwater, conversion of $CO_2$ into stable solid, liquid or non-greenhouse gases, permanent storage of $CO_2$ in liquid, solid or gaseous form, and the reuse of $CO_2$ to products.

11. The method of claim 1 wherein at least a part of said gaseous fuel stream or at least a part of said non-intermittent renewable fuel stream is used for combustion in an oxygen rich fuel combustion process.

12. The method of claim 1, wherein at least a part of said concentrated $CO/CO_2$ emissions is used in an oxygen rich fuel combustion process.

13. The method of claim 1 wherein said energy from said at least one intermittent renewable source is selected from the group consisting of wind and wind derived, solar and solar derived, aerothermal, tidal, off peak energy, waste thermal energy from industries and internal process exothermic reactions.

14. The method of claim 1 wherein said non-intermittent renewable electricity variations are within a range to maintain at least one of non-intermittent production of said oxygen stream, a hydrogen stream, said gaseous fuel stream, said gaseous intermediates stream, and said renewable fuel stream.

15. The method of claim 1 wherein at least a part of said energy from intermittent renewable sources comprises energy from stranded sources where no alternative energy distribution infrastructure exists.

16. The method of claim 1 wherein at least a part of said energy from intermittent renewable sources is stored before use.

17. The method of claim 1 further comprising the steps of:
 a. obtaining a renewable thermal energy from at least a part of said energy from intermittent renewable sources or at least a part of said gaseous fuel stream from said renewable carbonaceous feedstock; and
 b. producing said non-intermittent renewable fuel stream from at least a part of said renewable thermal energy.

18. The method of claim 1 wherein at least a part of said energy from at least one intermittent renewable source is stabilized by combining said energy from at least one intermittent renewable source with at least a part of said energy from said gaseous fuel stream prior to the generation of said non-intermittent renewable electricity.

19. The method of claim 1 wherein at least a part of said non-intermittent renewable electricity is generated by combining two or more independent intermittent renewable sources of energy.

20. The method of claim 1 wherein at least a part of said intermittent energy and non-intermittent renewable electricity is stored before use.

21. The method of claim 1 wherein at least a part of said non-intermittent renewable electricity is exchanged with an external electrical grid.

22. The method of claim 1 wherein at least a part of gaseous fuel from said gaseous fuel stream is stored before use.

23. The method of claim 1 wherein said oxygen stream is produced by at least one of a combination of oxygen separation from air and electrolysis of water.

24. The method of claim 1 wherein at least a part of oxygen from said oxygen stream is stored before use.

25. The method of claim 1 wherein at least a part of said non-intermittent renewable electricity is produced from process heat.

26. The method of claim 3 wherein at least a part of hydrogen from said hydrogen stream is combined with a stream selected from the group consisting of said gaseous fuel stream and said gaseous intermediates stream to maintain sufficient hydrogen to carbon ratio and calorific value of said streams.

27. The method of claim 3 wherein hydrogen in the said hydrogen stream is produced by processes selected from the group consisting of electrochemical hydrogen production processes, dehydrogenation of hydrocarbons process, biochemical hydrogen production process, photochemical hydrogen production process, thermochemical hydrogen production process and combinations thereof.

28. The method of claim 3 wherein at least a part of hydrogen from said hydrogen stream is stored before use.

29. The method of claim 1 wherein said renewable carbonaceous feedstock comprises a biomass.

30. The method of claim 1 wherein said renewable carbonaceous feedstock comprises at least one of waste materials and chemicals comprising carbon.

31. The method of claim 1 wherein at least a part of said gaseous intermediates stream and at least a part of said gaseous fuel stream comprise at least one of CO, $CO_2$, $CH_4$ and $H_2$.

32. The method of claim 1 wherein an adjustment to the gas composition of at least one of at least a part of said gaseous intermediates stream and at least a part of said gaseous fuel stream is done for efficient production of said non-intermittent fuel stream.

33. The method of claim 32 wherein said adjustment is achieved through at least one of processes comprising:
 a. adjustment of hydrogen from a hydrogen stream;
 b. adjustment of $CO/CO_2$ from said concentrated $CO/CO_2$ emissions;
 c. adjustment of oxygen from said oxygen stream to the production of said gaseous intermediates stream;
 d. adjustment of conditions in the production of said gaseous intermediates stream;
 e. adjustment of said non-intermittent renewable electricity to the production of said gaseous intermediates stream;
 f. adjustment of the composition of said renewable carbonaceous feedstock to the production of said gaseous intermediates stream; and
 g. adjustment by carrying out chemical reactions selected from the group consisting of reversible water gas shift reaction, Boudouard reaction, dry reformation reaction and electrochemical reduction.

34. The method of claim 1 wherein at least a part of said renewable carbonaceous feedstock comprises of at least a part of said gaseous fuel stream.

35. The method of claim 1 wherein the conversion of said gaseous intermediates stream to said renewable fuels is carried out by at least one of thermochemical reactions, electrochemical reactions, photochemical reactions and biochemical reactions.

36. The method of claim 1 wherein said renewable fuel stream comprises at least one of hydrocarbons, alcohols and ethers.

37. The method of claim 1 wherein the concentration of oxygen in said gaseous fuel stream and said gaseous intermediates stream is adjusted by regulating inflow of oxygen into the production process of said gaseous fuel stream and said gaseous intermediates stream.

38. The method of claim 37 wherein the concentration of oxygen in said gaseous fuel stream and said gaseous intermediates stream is not greater than 5% by volume.

39. The method of claim 29, wherein said biomass is selected from the group consisting of timber harvesting residues, soft-wood chips, tree branches, tree stumps, leaves, bark, sawdust, paper pulp, corn stover, lignin, wheat straw, switch grass, lupine, rice straw, sugarcane bagasse, miscanthus, grape pumice, almond shells, pecan shells, coconut shells, coffee grounds, grass pellets, and hay pellets.

40. The method of claim 30 wherein said waste materials and chemicals comprising carbon are selected from the group consisting of animal manure, municipal solid waste, municipal sewage, commercial waste, industrial chemical byproducts, glycerol from biodiesel production, used tires, card board, paper, plastic, rubber, black liquor, cloth, waste oil and biogas.

41. The method of claim 33, wherein said conditions comprise at least one of temperature and pressure.

42. The method of claim 36, wherein hydrocarbons, alcohols and ethers is selected from the group consisting of methanol, ethanol, higher alcohols, dimethyl ether, diesel, and other chemicals that are utilized as fuels or feedstock for chemical synthesis.

43. The method of claim 37, wherein the concentration of oxygen in said gaseous fuel stream and said gaseous intermediates stream is not greater than 2% by volume.

* * * * *